United States Patent [19]

Pytlewski et al.

[11] 4,417,977

[45] Nov. 29, 1983

[54] REMOVAL OF PCBS AND OTHER HALOGENATED ORGANIC COMPOUNDS FROM ORGANIC FLUIDS

[75] Inventors: Louis L. Pytlewski, Philadelphia, Pa.; Frank J. Iaconianni, Cherry Hill, N.J.; Kenneth Krevitz, Philadelphia, Pa.; Arthur B. Smith, Newark, Del.

[73] Assignee: The Franklin Institute, Philadelphia, Pa.

[21] Appl. No.: 429,096

[22] Filed: Sep. 30, 1982

[51] Int. Cl.[3] ...................... C07C 7/148; C07C 39/12; C10G 19/073; C10G 29/06

[52] U.S. Cl. ................................... 208/262; 252/581; 210/909; 585/469

[58] Field of Search ........................ 208/262; 252/581; 210/909; 585/469

[56] References Cited

U.S. PATENT DOCUMENTS

| | | | |
|---|---|---|---|
| 1,996,744 | 4/1935 | Britton | 260/154 |
| 2,448,092 | 9/1944 | Gibson | 260/683.4 |
| 2,449,088 | 9/1948 | Smith et al. | 280/396 |
| 2,914,558 | 11/1959 | Cooper | 260/521 |
| 3,075,021 | 1/1963 | Luvisi et al. | 260/650 |
| 3,188,357 | 6/1965 | Blumbergs | 260/655 |
| 3,239,568 | 3/1966 | De Pree et al. | 260/632 |
| 3,243,464 | 3/1966 | Parvi | 260/620 |
| 3,413,341 | 11/1968 | Bursack et al. | 260/521 |
| 3,595,931 | 7/1971 | Hay et al. | 260/668 |
| 3,686,337 | 8/1972 | Chang | 260/650 |
| 3,726,929 | 4/1973 | Payne et al. | 260/623 |
| 3,891,717 | 6/1975 | Gilbert et al. | 260/623 |
| 3,968,177 | 7/1976 | Kaufhold et al. | 260/638 |
| 4,001,340 | 1/1977 | Smith | 260/620 |
| 4,225,731 | 9/1980 | Marhold et al. | 568/775 |
| 4,284,516 | 8/1981 | Parker et al. | 210/757 |
| 4,301,083 | 11/1981 | Yoshimura et al. | 260/404 |
| 4,326,090 | 4/1982 | Smith et al. | 585/469 |
| 4,327,027 | 4/1982 | Howard | 270/340.3 |
| 4,353,793 | 10/1982 | Brunelle | 208/262 |
| 4,377,471 | 3/1983 | Brown et al. | 208/262 |
| 4,379,746 | 4/1983 | Norman et al. | 208/262 |

FOREIGN PATENT DOCUMENTS

| | | | |
|---|---|---|---|
| 1930341 | 12/1970 | Fed. Rep. of Germany | 568/730 |
| 255880 | 7/1926 | United Kingdom . | |
| 1068832 | 5/1932 | United Kingdom . | |
| 1995568 | 3/1935 | United Kingdom . | |
| 618189 | 2/1949 | United Kingdom | 570/226 |
| 1045298 | 10/1966 | United Kingdom | 568/710 |
| 1221019 | 2/1971 | United Kingdom | 568/796 |

OTHER PUBLICATIONS

A. Oku et al., Chemistry and Industry, pp. 841–842 (Nov. 1978).

Liggett, Analytical Chemistry, vol. 26, No. 4, pp. 748–750 (1954).

Pytlewski et al., 11th Mid-Atlantic Industrial Wastes Conference Jul. 15-17, 1979.

Pytlewski et al., Publication for EPA, 1980.

Furukawa et al., Markromol Chemistry, vol. 38, pp. 244–247 (1960).

Toke et al., Acta Chim, Acad. Sci. Hung., vol. 93(3–4), pp. 421–424 (1977).

Toke et al., Acta Chim. Acad. Sci. Hung., vol. 100(1–4), pp. 257–264 (1979).

W. H. Dennis et al., Bulletin of Environmental Contamination and Toxicology, vol. 14, No. 6, pp. 736–744 (1975).

P. Johncock et al., Analytical Chemistry, vol. 94, pp. 245–247 (1959).

*Primary Examiner*—John E. Kittle
*Assistant Examiner*—Robert A. Wax
*Attorney, Agent, or Firm*—Dann, Dorfman, Herrell and Skillman

[57] ABSTRACT

Organic functional fluids containing halogenated organic compounds present as contaminants therein are treated with a NaPEG decomposition reagent in an inert atmosphere to produce a functional fluid phase substantially free of the halogenated organic compound and a reagent residue phase containing a partially dehalogenated organic derivative therein. The latter may be further dehalogenated by reacting the reagent residue with oxygen.

11 Claims, No Drawings

REMOVAL OF PCBS AND OTHER HALOGENATED ORGANIC COMPOUNDS FROM ORGANIC FLUIDS

BACKGROUND OF THE INVENTION

The present invention relates generally to a method for removing halogenated organic compounds from organic fluids containing same and more particularly to a method for removing PCBs from functional fluids, such as transformer oil, contaminated therewith.

The potential hazard to health and the environment posed by synthetic halogen-containing organic chemicals is well known. Compounds such as polychlorinated biphenyls (PCBs), dichlorodiphenyltrichloroethane (DDT), decachlorooctahydro-1,3,4-metheno-2H-cyclobuta-[c,d]-pentalen-2-one (Kepone®), and 2,4,5-trichlorophenoxyacetic acid, (2,4,5-T), although having demonstrated utility, have been found to be persistent environmental toxins which require safe and effective means of disposal.

Halogenated organic compounds present a difficult disposal problem because of the highly stable nature of the carbon-halogen bonds present therein. The bond energy of a carbon-chlorine bond, for example, is on the order of eighty-four kcal./mole. Thus, many halogenated organic compounds are not only resistant to biodegradation, they cannot be degraded in a practical and effective manner by way of the well known chemical decomposition methods. In most cases, known detoxifying methods such as chlorolysis, catalytic dehydrohalogenation, molten salt reactions, ozone reactions and alkali metal reduction achieve only partial dehalogenation. Moreover, these prior art methods typically involve one or more drawbacks, such as the use of expensive reagents, extensive temperature control, inert atmospheres, complex apparatus, substantial energy consumption and the like.

A particularly troublesome problem is presented when the halogenated organic compound is present as a contaminant in an otherwise useful functional fluid. For instance, PCBs were once widely used as a dielectric fluid in electrical equipment such as transformers and capacitors because of their excellent insulating properties. In 1977, however, all production of PCBs was stopped due to their cumulative storage in human fatty tissue and reports of extremely high toxicity. PCBs were replaced as a dielectric fluid with other less harmful substances. These latter substances have since been found to contain residual amounts of PCBs therein. Consequently, the maintenance, operation and disposal of PCB-contaminated transformers and transformer oil is now strictly regulated.

Since the production ban on PCBs, incineration has probably been the most widely used method for destroying PCBs and PCB--contaminated materials. Disposal by incineration is decidedly wasteful, however, since potentially recyclable materials, such as functional fluids, are destroyed in the process. To avoid such waste, methods have been proposed whereby PCB-contaminated materials in particular would be treated with an adsorbant, e.g., by passing the material through a bed of activated charcoal or resin to selectively remove the PCBs from said material. Although PCBs are physically removed from the recyclable material in this manner, the disposal of adsorbed PCBs still remains a problem.

During the past several years, there has been developed at the Franklin Research Center of the Franklin Institute, Philadelphia, Pennsylvania, a system for stripping the chlorine substituents from various halogenated organic compounds, including PCBs, thus rendering them non-toxic and readily disposable. More specifically, Pytlewski, Krevitz and Smith, in their U.S. patent application Ser. No. 158,359, filed June 11, 1980, now U.S. Pat. No. 4,337,368, disclose and claim a method for the decomposition of halogenated organic compounds, which represents a significant advance over the aforementioned decomposition methods of the prior art. The decomposition reagent used in practicing the method of Pytlewski et al. is formed from the reaction between an alkali metal, a liquid reactant, such as polyglycol or a polyglycol monoalkyl ether, and oxygen. This reagent produces virtually complete dehalogenation simply by mixing it with the halogenated compound in the presence of oxygen.

In U.S. patent application Ser. No. 240,622, filed Mar. 5, 1981, there is described and claimed another invention by Pytlewski et al. based on the discovery that decomposition of halogenated organic compounds may be carried out using a reagent produced by the reaction of an alkali metal hydroxide (rather than an alkali metal), a liquid reagent, such as a polyglycol or a polyglycol monalkyl ether, and oxygen. This decomposition reagent gives results which are comparable to those obtained with the method described in the earlier filed application of Pytlewski et al. referred to above.

The decomposition reagents of the aforesaid patent applications are collectively referred to hereinafter as NaPEG reagents, or simply NaPEG, and the expression "decomposition reagent", as used herein, refers to these NaPEG reagents.

The development of the NaPEG reagents has made it possible to remove various halogenated organic compounds, including PCBs, from fluids contaminated therewith, as well as to decompose such compounds in concentrated form in a safe, efficient and effective manner. However, as disclosed in our aforementioned patent applications, it was believed, prior to the present invention, that in order for decomposition to occur using NaPEG it was essential that the decomposition reaction be carried out in the presence of oxygen, since attempts at operating in an inert atmosphere were found to be unsuccessful.

SUMMARY OF THE INVENTION

It has now been discovered, in accordance with the present invention that organic functional fluids may be rendered substantially free of organic halogenated compounds present as contaminants therein, by treating the functional fluid with a NaPEG decomposition reagent in an inert atmosphere.

According to the present invention, halogenated organic compounds are removed from an organic functional fluid containing same in an efficient and effective manner by treating the functional fluid with a NaPEG reagent under conditions producing reaction between the NaPEG and the halogenated organic compound to form a partially dehalogenated derivative, the solubility which is such that it is readily separable from the functional fluid. Partial dehalogenation is achieved simply by vigorous mixing of the fluid containing the halogenated organic compound with a NaPEG reagent under reactive conditions in an inert atmosphere. In general, the reagent residue (i.e. NaPEG reaction products and any unreacted NaPEG left after reaction) is substantially immiscible with the functional fluid, and the solubility characteristics of the reagent residue and the partially dehalogenated derivative are such that the derivative is more soluble in the reagent residue than in the functional fluid. The mixture thereafter separates into a two-phase system comprising a functional fluid phase substantially free of halogenated organic compounds and a NaPEG reagent residue phase containing said partially dehalogenated derivative.

The partially dehalogenated derivative present in the reagent residue may be reacted further with oxygen to effect substantially complete dehalogenation of the starting halogenated organic compound. The principal products of this reaction are sodium chloride and various oxygenated derivatives of the starting halogenated organic compound. These latter substances are easily disposable under environmentally safe conditions.

In addition to providing an efficient and effective way for removing substantially all of the halogenated organic contaminant contained in a functional fluid containing the same, this improved method possesses other notable advantages. For example, as in the earlier decomposition methods using the NaPEG reagents, it does not require highly specialized equipment or involve extreme operating conditions. The partial dehalogenation is accomplished by merely reacting, under an inert atmosphere, the NaPEG reagent with the halogenated organic compound present in the functional fluid. Moreover, it has been found that the partially dehalogenated derivative formed as a result of the reaction will, when further treated with NaPEG and oxygen, react more quickly to form the substantially complete dehalogenated product than would the starting halogenated organic compound. This is due to the electron configuration modification of the halogenated organic compound which occurs during partial dehalogenation. Therefore, when the partially dehalogenated derivative present in the reagent residue is subjected to further decomposition treatment involving reaction with oxygen, e.g., using NaPEG reagent, substantially complete dehalogenation of the derivative occurs quite rapidly. This is an important factor from the standpoint of application of the invention on a commercial scale.

Another significant advantage of the present invention is that it obviates repeated aqueous extractions with an aqueous extraction medium to remove the decomposition products from the functional fluid as is required in some prior art processes in which complete dehalogenation of the halogenated organic compound occurs in the functional fluid. In the method of the present invention, functional fluid substantially free of halogenated organic contaminants is obtained in a treatment, which, in effect, involves only a single extraction.

The use of an inert atmosphere in carrying out the mixture of the present invention also provides certain advantages. For example, oxygen, water and carbon dioxide tend to react with the decomposition reagent, particularly above room temperature. Hence, the exclusion of air allows more efficient use of the reagent. Furthermore, the exclusion of oxygen is beneficial in large scale processing where temperatures in excess of the flash point of the functional fluid are desirable. Unlike our earlier decomposition methods a closed system is required in practicing the method of the present invention.

DESCRIPTION OF THE INVENTION

In preparing the NaPEG reagent, which acts to partially dehalogenate the halogenated organic compound, any of the alkali metals or alkali metal hydroxides may be used as the first reactant. Lithium, sodium, and potassium, or their hydroxides, are preferred because of their ready availability and relatively low cost. Of these, sodium or sodium hydroxide is particularly preferred because it is less expensive than the others and produces a highly reactive reagent. Mixtures of different alkali metals or alkali metal hydroxides may be used if desired.

A second reactant required for the production of the decomposition reagent is a compound having the general formula:

$$HO\,[(\overset{R_1}{\underset{R_2}{C}})_x-O-]_n\,R,$$

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400, and x has a value of at least 2, which includes polyglycols and polyglycol monoalkyl ethers. The lower alkyl radical in the foregoing formula may be methyl, ethyl, propyl, isopropyl, butyl or isobutyl. The cycloalkyl radical may be cyclopentyl, cyclohexyl, cycloheptyl, and cyclooctyl. The aryl radical may be phenyl, benzyl, biphenyl or napthyl. The substituents on the $R_1$ and $R_2$ radicals include, but are not limited to, lower alkyl, e.g. methyl, ethyl, propyl, butyl, and isobutyl; halo, e.g. chloro or bromo; nitro; sulfato; carboxyl; amino; mono- and di-lower-alkyl amino, e.g. methylamino, ethylamino, dimethylamino or methylethylamino; amino; hydroxy; and lower alkoxy, e.g. methoxy or ethoxy.

Suitable reactants falling within the above formula include diethylene glycol, diethylene glycol monoethyl ether, polyether glycols, such as polyethylene glycols, polypropylene glycols and polybutylene glycols and related long chain glycol monoalkyl ethers. The preferred reactants are those of the above general formula wherein $R_1$ and $R_2$ are hydrogen and x is 2. Particularly preferred are polyethylene glycols, i.e. polymers of formula $HO[CH_2\text{-}CH_2\text{-}O]_nH$, having an average molecular weight range from about 100 to about 20,000. The above described reactants may be either liquids or solids. Those which are solids, e.g. the high molecular weight polyethylene glycols, should be melted before preparation of the decomposition reagent is begun. Neither low volatility, non-polar liquids, nor glycolic liquids in which both terminal hydroxyl groups are alkylated has been found to produce the desired decomposition.

The term "polyglycols", as used herein, refers to polymers of dihydric alcohols.

Oxygen has been determined to be a necessary third reactant for reagent formation. When the alkali metal or alkali metal hydroxide and a compound of the above general formula are reacted in the presence of oxygen, the formation of the reagent is readily observable, as the reaction mixture, which is initially clear, takes on a dark amber color. This color change does not occur in the absence of oxygen. For example, the reaction of sodium hydroxide with polyethylene glycol in a nitrogen atmosphere produces a solution that is virtually clear and ineffective as a reagent. However, when oxygen is thereafter introduced into the resultant solution, the decomposition reagent will be formed, as indicated by the aforementioned color change. Thus, the required reactants may be reacted simultaneously, or according to the two-step procedure just described.

The reaction for forming the reagent proceeds spontaneously at room temperature simply by mixing the reactants in an open reaction vessel, preferably with stirring. It is unnecessary to bubble oxygen into the reaction mixture, for atmospheric oxygen satisfies the requirements of the reaction. Thus, no temperature control or specialized equipment is required for carrying out the reaction.

The decomposition reagents are basic substances possessing polyethylene glycol moieties $(CH_2CH_2—O)_n$ and hydroxyls (OH). These are ideal chemical structures for the solvation of metal cations, which serves to activate the basic species. Moreover, these decompositions reagents are highly soluble in or miscible with halogenated organic compounds such as PCBs.

The present invention may be practiced on various functional fluids contaminated with widely varying amounts of halogenated organic compounds. The present invention is particularly useful for removing halogenated organic compounds such as PCBs from either non-polar fluids such as transformer oils or relatively aprotic polar fluids such as dimethylformamide, dimethyl sulfoxide, N-methyl-2-pyrrolidone, various ethers, and the like. Although the present invention may be practiced on protic polar fluids, it would require much more of the dehalogenation reagent to achieve the desired results due to reaction of the protic polar fluid with the dehalogenating reagent itself. A more economical approach is to extract the halogenated organic compound from the protic polar fluid using a non-polar extractant such as hexane. The contaminated extractant containing the halogenated organic compound could then be treated according to the method of the present invention.

In order to achieve the partial dehalogenation and removal of the partially dehalogenated organic compound from the functional fluid containing the same in accordance with this invention, all that is necessary is to mix vigorously the fluid containing the halogenated organic compound with NaPEG reagent in an inert atmosphere under reactive conditions. The mole ratio of NaPEg to halogenated organic substance will depend on whether the present invention is practiced on a halogenated organic compound in relatively concentrated form or a functional fluid which is contaminated with a halogenated organic compound. When practiced on a halogenated organic compound in concentrated form the mole ratio of NaPEG to halogen atoms present in the halogenated organic compound should be about one to one, or greater. When practiced on a functional fluid contaminated with small amounts (ppm) of a relatively small amount of halogenated organic compound the ratio of NaPEG to halogen atoms present must be empirically determined, however, a ratio of 10 moles NaPEG to 1 mole of contaminated fluid has been found to cover a broad range of halogenated organic compound concentrations.

While the partial dehalogenation reactions will occur at room temperature, the mixture may be heated to speed the rate of reaction. Heating to a temperature in the range of about 25° C. to 125° C. has been found to produce satisfactory results when the halogenated compound was PCB and the functional fluid was dielectric fluid or transformer oil. Of course, the temperature may vary depending upon the nature of the reagent used, the halogenated organic compound being removed and the functional fluid in which the halogenated organic compound is present.

Although the reaction mechanism on which the present invention is based is not completely understood, it is believed that the halogens removed in the partial dehalogenation step are replaced by oxygenated groups such as ethers and/or hydroxyls. This partially dehalogenated derivative is therefore more polar than the starting halogenated organic compound, and thus, it is more soluble in the reagent residue and less soluble in the functional fluid. Consequently, the process results in extraction of the partially dehalogenated derivative from the functional fluid.

In accordance with the present invention, the above-described decomposition reagent serves two functions. First, it functions in an inert atmosphere as a decomposition or dehalogenating reagent effecting not complete dehalogenation, but partial dehalogenation. This is thought to be due to the absence of air and specifically oxygen, water and carbon dioxide. Second, it functions as an extractant, extracting the partially dehalogenated derivative from the functional fluid into the reagent residue. This is due to the fact that the now partially dehalogenated organic compound is more soluble and miscible in the reagent residue than in the original functional fluid.

Substitution of an inert atmosphere for air results in the formation of the partially dehalogenated derivative rather than the substantially complete dehalogenated derivative, as in the earlier NaPEG decomposition processes. As mentioned above, it is the partially dehalogenated derivative and other reaction products produced in its formation which are extracted into the reagent residue phase. The inert atmosphere provides the appropriate environment for the partial dehalogenation. The use of nitrogen, helium, or argon, as the inert atmosphere, is suitable in the process. However, other inert atmospheres may also be employed in practicing the invention.

After treatment of the functional fluid with the NaPEG reagent under conditions referred to above, the mixture is allowed to separate into a two-phase system comprising a reagent residue phase containing the partially dehalogenated derivative and a functional fluid phase substantially free of halogenated organic compounds which may then be drawn off and reused by simple decantation.

In order to render the contaminants removed from the functional fluid non-toxic, further treatment may be required, as would be the case where the original halogenated compound was a polychlorinated biphenyl. As disclosed in the above-mentioned patent and application, reacting the NaPEG reagents with a halogenated organic compound and oxygen effects substantially complete dehalogenation of the halogenated organic compound and forms an oxygenated derivative of said compound. It has been found that the partially dehalogenated derivative obtained according to the present invention, is more reactive with oxygen and NaPEG reagent than the starting halogenated organic compound. For instance, PCBs from which one or two chlorines have been removed react with oxygen in the presence of NaPEG reagent very rapidly to form an oxygenated biphenyl derivative. The reaction for producing the completely dehalogenated derivative proceeds by stirring the reactants in an open reaction vessel. It is unnecessary to bubble oxygen or air into the reaction vessel, although this will accelerate the reaction. Further treatment of the partially dehalogenated contaminant may include the use of other known methods used to detoxify such materials, as well as the use of the NaPEG reagent, as described above. The oxygenated derivatives obtained from the further decomposition treatment are readily recovered and may be converted into useful products, e.g. polymer starting materials, anti-oxidants and plasticizers, by procedures well known to those skilled in the art. Considering that reusable products may be obtained from the invention as disclosed herein, at least a portion of the operating costs of the present method should be recoupable.

Representative halogenated organic compounds present in functional fluids which can be partially dehalogenated and removed therefrom in accordance with the present invention are: hexachlorocyclohexene, hexachlorobenzene, trichlorobenzene, tetrachlorobenzene, dichlorophenol, pentachlorophenyl, dichlorodiphenyltrichloroethane, decachloro-octahydro-1,3,4-metheno-2H-cylobuta-[c,d]-pentalen-2-one and polychlorinated biphenyl.

The invention will be further understood by reference to the following example, which is intended to illustrate, and not to limit the invention.

EXAMPLE 1

Removal of PCBs From Hydrocarbon-Based Transformer Oils Containing the Same

A decomposition reagent was prepared from sodium and polyethylene glycol (MW of 400) and oxygen, as described in Example 1 of U.S. Pat. No. 4,337,368. A 60 ml sample of transformer oil containing approximately 652 parts PCBs per million was placed in a flask and heated with stirring to approximately 125° C. To the flask was added 2 mls of decomposition reagent heated to about 80° C. The mixture was stirred vigorously at about 125° C. for approximately 2 hours under a nitrogen blanket. The reaction mixture was allowed to cool to room temperature, and a separation of the reaction mixture into two phases was observed. An aliquot of oil was taken from the transformer oil phase and analyzed for remaining PCBs content by gas chromatography/electron capture (g.c./e.c.). This analysis showed that 27 ppm of PCB remained in the treated oil.

Treatment of the reagent residue phase, by heating to 150° C. in the presence of air ($O_2$) yields a mixture entirely free from PCB.

As those skilled in the art will appreciate, the present invention provides a very effective and efficient way of removing halogenated organic compounds from otherwise useful fluids, and recycling such fluids.

While the method herein described constitutes a preferred embodiment of the invention, it is to be understood that the invention is not limited to the precise embodiment of the described method, but that changes may be made herein without departing from the spirit and scope of the invention, as set forth in the appended claims.

What is claimed is:

1. A method for the removal of a halogenated organic compound from an organic fluid containing said compound, comprising the steps of:

(a) providing a reagent comprising the product of the reaction of a first reactant selected from the group consisting of an alkali metal or an alkali metal hydroxide, a second reactant having the general formula $$HO[(\overset{R_1}{\underset{R_2}{C}})_x-O-]_n-R,$$

wherein R is hydrogen or lower alkyl, $R_1$ and $R_2$ are the same or different and are selected from the group consisting of hydrogen, unsubstituted or substituted lower alkyl, unsubstituted or substituted cycloalkyl having from 5 to 8 carbon atoms, and unsubstituted or substituted aryl, n has a value from about 2 to about 400 and x has a value of at least 2, and oxygen as a third reactant;

(b) mixing said reagent with said fluid containing said halogenated compound in an inert atmosphere under reactive conditions to form a derivative of said halogenated organic compound having a reduced halogen content and a reagent residue, the reagent residue being substantially immiscible with said fluid, and said derivative being more soluble in said reagent residue than in said fluid;

(c) allowing said mixture to separate into a two-phase system comprising a reagent residue phase containing said derivative and a fluid phase substantially free of said halogenated compound; and (d) separating said reagent residue phase from said fluid phase.

2. The method of claim 1 wherein (i) said decomposition reagent is formed from a first reactant selected from the group consisting of lithium, sodium, potassium, or the hydroxides of said metals, or mixtures of said metals or said hydroxides, a second reactant having the formula set forth in claim 1 wherein $R_1$ and $R_2$ are hydrogen and x is 2, and oxygen as a third reactant, and (ii) said halogenated organic compound is selected from the group consisting of hexachlorocyclohexane, hexachlorobenzene, trichlorobenzene, tetrachlorobenzene, dichlorophenol, pentachlorophenol, dichlorodiphenyltrichloroethane, decachlorooctahydro-1,3,4-metheno-2H-cyclobuta-[c,d]-pentalen-2-one and polychlorinated biphenyl.

3. The method of claim 1 wherein said first reactant is sodium and said second reactant is polyethylene glycol.

4. The method of claim 3 wherein the halogenated organic compound is polychlorinated biphenyl.

5. The method of claim 1 wherein said inert atmosphere consists essentially of nitrogen, helium or argon.

6. The method of claim 1 wherein said fluid containing said halogenated organic compound comprises a non-polar fluid in which said halogenated organic compound is miscible.

7. The method of claim 6 wherein said non-polar fluid comprises a hydrocarbon-based oil.

8. The method of claim 1 wherein said fluid containing said halogenated organic compound comprises an aprotic polar fluid in which said halogenated compound is miscible.

9. The method of claim 1 including the step of further treating said derivative of reduced halogen content in said reagent residue phase with a decomposition reagent to effect substantially complete dehalogenation of said derivative.

10. The method of claims 9 wherein said further treatment comprises reacting said derivative of reduced halogen content in the presence of oxygen with a decomposition reagent formed from a first reactant selected from the group consisting of lithium, sodium, potassium, or the hydroxides of said metals, or mixtures of said metals or said hydroxides, a second reactant having the formula set forth in claim 1 wherein $R_1$ and $R_2$ are hydrogen and x is 2, and oxygen as a third reactant.

11. The method of claim 10 wherein said alkali metal is sodium and said second reactant is polyethylene glycol.

* * * * *